United States Patent [19]

Johnson

[11] Patent Number: 5,041,097

[45] Date of Patent: Aug. 20, 1991

[54] INTRAVENOUS CATHETER FITTING WITH PROTECTIVE END SEAL

[76] Inventor: Gerald W. Johnson, 17115 Red Oak, Suite 211, Houston, Tex. 77090

[21] Appl. No.: 485,285

[22] Filed: Feb. 26, 1990

[51] Int. Cl.⁵ ............................................. A61M 5/178
[52] U.S. Cl. .................................... 604/167; 604/169; 604/264
[58] Field of Search ............... 604/167, 169, 278, 164, 604/256, 264, 280, 273, 244

[56] References Cited

U.S. PATENT DOCUMENTS

| | | | |
|---|---|---|---|
| 3,097,646 | 12/1960 | Scislowicz | 604/167 |
| 4,106,491 | 8/1978 | Guerra | 604/167 |
| 4,338,934 | 7/1982 | Spademan | 604/167 |
| 4,585,440 | 4/1986 | Tehervenkov et al. | 604/167 |
| 4,817,631 | 4/1989 | Schnepp-Pesch et al. | 604/167 |
| 4,904,240 | 2/1990 | Hoover | 604/167 |
| 4,954,130 | 9/1990 | Edwards | 604/169 |

FOREIGN PATENT DOCUMENTS 2192793  7/1987  United Kingdom ................ 604/167

Primary Examiner—John D. Yasko
Assistant Examiner—Kathleen A. Daley
Attorney, Agent, or Firm—Neal J. Mosely

[57] ABSTRACT

An intravenous catheter has an elongate small diameter flexible tubular front portion and a rear base portion which has an interior bore in communication with the interior of the tubular portion for connection to a needle or other fluid injection or withdrawal members. A thin flexible membrane seal formed of resilient stretchable material is secured over the opening at the rear of the catheter base. The elasticity of the membrane seal allows the beveled front end of a needle to be pushed through the membrane and puncture the seal as it passes through and will not tear, but will stretch as the forward motion of the needle continues and conform to the profile of front portion of the needle base and allow it to engage the interior of the catheter base. The needle may be inserted into the catheter in the usual manner and the needle and catheter may be used just as any standard catheter-needle assembly. When the needle is withdrawn from the catheter, the membrane seal resumes its original position, except that it has a very tiny hole where the needle penetrated. Under normal use conditions, the resilient material of the membrane seal will close the hole to a diameter so small that no leakage occurs. Thus, the membrane seal prevents fluid, i.e., blood, from leaking from the catheter until such time as the connection is made at the base to complete the fluid injection or withdrawal procedure.

10 Claims, 1 Drawing Sheet 5,041,097

INTRAVENOUS CATHETER FITTING WITH PROTECTIVE END SEAL

BACKGROUND OF THE INVENTION

1. Field of the Invention

This invention relates generally to catheter fittings which are adapted to inject substances into humans and animals and/or to withdraw specimens therefrom, and more particularly to a catheter fitting having a protective end seal at the connection end for preventing fluid leakage during installation, connection, and use.

2. Brief Description of the Prior Art

Catheters are hollow tubular devices which are inserted into a cavity, duct, vessel, or vein to permit injection or withdrawal of fluids from a patient. Existing catheters are commonly provided in a sterile package assembled with a catheter needle inside the catheter and an end plug in the back end of the needle. A tubular manually removable protective sheath covers the forward end of the needle and catheter.

The catheter has an elongate small diameter flexible tubular front portion and an enlarged diameter rear portion or base portion at the back end in which has an interior bore in communication with the interior of the tubular portion. The exterior of the catheter base may be provided with a small radial flange or other conventional configuration. The interior bore of the catheter base portion may be smooth or may have conventional Leur lock threads for connecting the catheter to various intravenous tubular members when the needle is removed.

The catheter needle has a hollow tubular needle body with a beveled front end to facilitate hypodermic and intravenous insertion and has a tubular base portion at the back end in communication with the interior bore of the needle. The exterior of the needle base portion may be provided with a bead or otherwise configured to receive a protective sheath. The rear portion of the needle base has an interior bore which usually is provided with plug slidably received therein. The plug has a reduced diameter forward portion which may be tapered to frictionally engage the bore at the rear end of the needle and an enlarged diameter rear portion which has flat surfaces on the exterior to facilitate griping with the fingertips to remove the plug. The plug is also usually provided with a small interior bore.

In the assembled and packaged condition, the needle is installed in the catheter with its base member engaged in the interior bore of the catheter base and the plug frictionally engaged in the bore at the rear end of the needle. The protective sheath is received over the catheter and engaged on the larger diameter of the needle base. The interior diameter of the catheter tubular front portion closely surrounds the forward portion of the needle but allows axial sliding movement of needle therethrough. The length of the catheter tubular portion is slightly shorter than the length of the needle so that the beveled front end of the needle is exposed to facilitate intravenous insertion of both the needle and flexible tubular portion of the catheter. A removable tubular protective sheath is received on the needle base and the forward portion of the needle and catheter and has an enclosed front end to prevent accidental pricking by the needle.

In using the conventional catheter, the catheter assembly is removed from its package and the protective sheath is removed. The beveled end of the needle having the tubular portion of the catheter surrounding its length is inserted into the vein. When the vein is penetrated, blood will flow into the needle and will be visible in the base portion of the needle and will also be drawn into the small bore of the plug due to capillary action. This detection of the fluid will signal that a suitable penetration has been made.

While the catheter is held stationary, the plug is removed from the needle or the needle is withdrawn from the catheter. The person installing the catheter must then connect another tubular fitting to the open rear end of the needle or the catheter to complete the fluid injection or withdrawal procedure. However, between the time the plug is removed from the needle or the needle is withdrawn from the catheter and the open end is connected, the body fluids will continue to flow unobstructed through the catheter and/or needle. This unnecessary flow presents many problems.

One problem arises because the person installing the catheter must hold the catheter stationary with one hand and remove the plug from the needle or withdraw the needle from the catheter with the other hand and then effect the connection. Thus, there is exposure to the free flowing body fluids during the interval between the time the plug is removed from the needle or the needle is withdrawn from the catheter and the open end is connected.

Another problem is that the person installing the catheter must very quickly remove the plug from the needle or withdraw the needle from the catheter with only one hand available. Often, the removed plug or needle will be haphazardly placed on the nearest convenient surface while connecting another tubular fitting to the open rear end of the needle or the catheter. As a result, the cap or needle may be lost in the bed covers or on the floor so there is exposure to both contaminated body fluids and to an exposed needle which could result in accidental pricking by the needle. Thus, the person installing the catheter, the patient, others in the room, and even hospital personnel cleaning the room or the bed linens are exposed.

The unnecessary leakage of body fluids is of critical concern to health practitioners from the standpoint of both handling the catheter and the needle during installation and removal and the disposal of used catheters and needles. Accidental exposure to some contaminated body fluids can have very serious and even fatal health consequences. For example, the body fluid may be contaminated with diseases such as hepatitis or A.I.D.S.

It would therefore be desirable to provide a catheter which would automatically seal at the open end to prevent fluid leakage when a needle or fitting is removed and would still allow connection of the catheter to other devices with the seal in place. Such a device would allow sufficient time for the person installing the catheter to properly shield and dispose of the needle with a minimum of handling and in a reliable and efficient manner to provide protection from accidental exposure to contaminated body fluids and puncture from lost needles.

There are many devices for shielding a hypodermic needle against accidental puncture and for covering the needle for disposal. However, there is no known commercially available catheter having a protective seal which eliminates the problems discussed above.

The present invention is distinguished over the prior art in general, and these patents in particular by an intravenous catheter which has an elongate small diameter flexible tubular front portion and a rear base portion which has an interior bore in communication with the interior of the tubular portion for connection to a needle or other fluid ejection or withdrawal members. A thin flexible membrane seal formed of resilient stretchable material is secured over the opening at the rear of the catheter base. The elasticity of the membrane seal allows the beveled front end of a needle to be pushed through the membrane and puncture the seal as it passes through and will not tear, but will stretch as the forward motion of the needle continues and conform to the profile of front portion of the needle base and allow it to engage the interior of the catheter base. The needle may be inserted into the catheter in the usual manner and the needle and catheter may be used just as any standard catheter-needle assembly. When the needle is withdrawn from the catheter, the membrane seal resumes its original position, except that it has a very tiny hole where the needle penetrated. Under normal use conditions, the resilient material of the membrane seal will close the hole to a diameter so small that no leakage occurs. Thus, the membrane seal prevents fluid from leaking from the catheter until such time as the connection is made at the base to complete the fluid injection or withdrawal procedure.

SUMMARY OF THE INVENTION

It is therefore an object of the present invention to provide an intravenous catheter fitting having a protective sealing membrane covering the connection end which will automatically prevent fluid from leaking from the fitting.

It is another object of this invention to provide an intravenous catheter fitting having a protective sealing membrane covering the connection end which facilitates the safe, quick, and easy installation and removal of a needle or other device onto and out of the intravenous tubular catheter while the seal remains in place.

Another object of this invention to provide an intravenous catheter fitting having a protective sealing membrane covering the connection end which automatically prevents fluid from leaking from the fitting after it has been placed into a vein, before and after a secure end connection has been made, and after the end connection has been disconnected.

Another object of this invention is to provide an intravenous catheter fitting having a protective sealing membrane covering the connection end which automatically covers the connection end of the catheter to prevent fluid leakage in the event of accidental retraction of the end connection.

Another object of this invention is to provide an intravenous catheter fitting having a protective sealing membrane covering the connection end which will allow sufficient time for the person installing the catheter to properly shield and dispose of the needle used in conjunction with the installation with a minimum of handling and in a reliable and efficient manner to provide protection from accidental exposure to contaminated body fluids and puncture from lost needles.

A further object of this invention is to provide an intravenous catheter fitting having a protective sealing membrane covering the connection end which does not require modifications to the syringe or other instruments to which it is attached.

A still further object of this invention is to provide an intravenous catheter fitting having a protective sealing membrane covering the connection end which is simple in-design and construction, economical to manufacture, and rugged and reliable in use.

Other objects of the invention will become apparent from time to time throughout the specification and claims as hereinafter related.

The above noted objects and other objects of the invention are accomplished by an intravenous catheter which has an elongate small diameter flexible tubular front portion and a rear base portion which has an interior bore in communication with the interior of the tubular portion for connection to a needle or other fluid ejection or withdrawal members. A thin flexible membrane seal formed of resilient stretchable material is secured over the opening at the rear of the catheter base. The elasticity of the membrane seal allows the beveled front end of a needle to be pushed through the membrane and puncture the seal as it passes through and will not tear, but will stretch as the forward motion of the needle continues and conform to the profile of front portion of the needle base and allow it to engage the interior of the catheter base. The needle may be inserted into the catheter in the usual manner and the needle and catheter may be used just as any standard catheter-needle assembly. When the needle is withdrawn from the catheter, the membrane seal resumes its original position, except that it has a very tiny hole where the needle penetrated. Under normal use conditions, the resilient material of the membrane seal will close the hole to a diameter so small that no leakage occurs. Thus, the membrane seal prevents fluid from leaking from the catheter until such time as the connection is made at the base to complete the fluid injection or withdrawal procedure.

DESCRIPTION OF A PREFERRED EMBODIMENT

Figure 1:
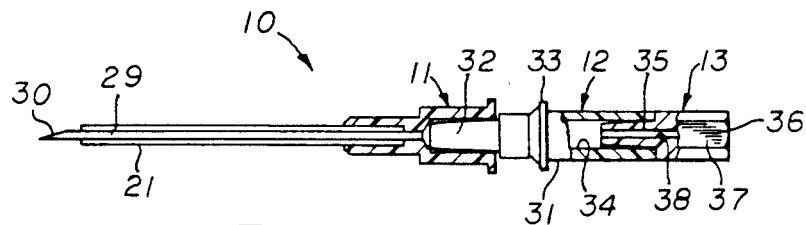
FIG. 1 is a longitudinal cross section of a standard intravenous catheter assembly of the prior art.

Referring to the drawings by numerals of reference, there is shown in FIG. 1, a standard intravenous catheter needle assembly of the prior art designated generally by numeral 10. Existing catheters 11 are commonly provided in a sterile package assembled with a catheter needle 12 slidably received inside the catheter and an end plug 13 frictionally engaged in the back end of the needle. A tubular, manually removable protective sheath (not shown) usually covers the forward end of the needle and catheter. The interior diameter of the catheter tubular front portion closely surrounds the forward portion of the needle but allows axial sliding movement of needle therethrough. The length of the catheter tubular portion is slightly shorter than the length of the needle so that the beveled, pointed front end of the needle is exposed to facilitate intravenous insertion of both the needle and flexible tubular portion of the catheter.

Figure 2:
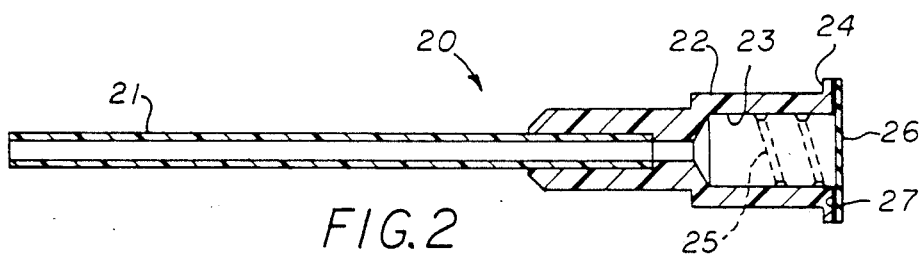
FIG. 2 is a longitudinal cross section, in larger scale, of the present intravenous catheter fitting having a protective membrane seal covering the connection end.

As shown in enlarged detail in FIG. 2, the present catheter 20 has an elongate small diameter flexible tubular front portion 21 and an enlarged diameter rear portion or base portion 22 at the back end in which has an interior bore 23 in communication with the interior of the tubular portion 21. The exterior of the catheter base 22 may have a small radial flange 24 or other conventional configuration. The interior bore 23 of the present catheter base portion may be smooth or may have conventional Leur lock threads 25 for connecting the catheter 20 to the needle or various other intravenous tubular members when the needle 12 is removed.

Figure 3:
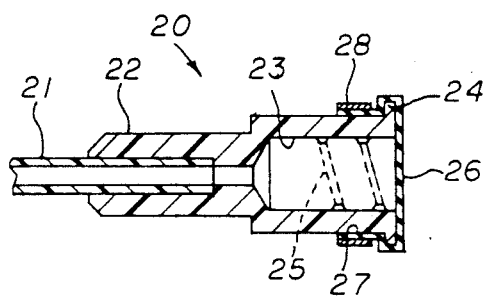
FIGS. 3 and 4 are partial longitudinal cross sections of the present intravenous catheter showing alternate methods of securing the protective membrane seal to the connection end of the catheter base.
Figure 4:
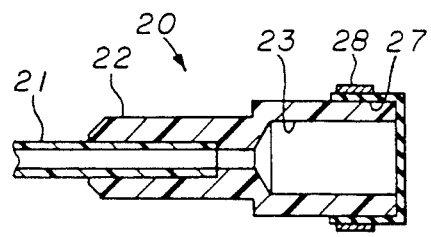

A thin flexible membrane 26 seal formed of resilient stretchable elastomeric material, preferably latex, is secured over the opening at the rear of the catheter base 22. As seen in FIG. 2, on catheters having a radial flange surrounding the opening, the membrane seal 26 may be secured to the flange face by suitable means such as adhesive 27, epoxy, or other conventional means compatible with the catheter base and membrane material. As seen in FIG. 3, the membrane seal 26 may also be secured to the exterior of the base 22 to cover the flange and opening 23 of the base 22. As seen in FIG. 4, on catheters not having a flanged end, the membrane seal 26 may be secured on the exterior of the base 22 to cover the opening 23. The membrane seal 26 may be secured with adhesive 27, epoxy, etc., and/or may be clamped onto the base exterior by means of a ring-like clamp 28 or other conventional fastener.

Referring again to FIG. 1, the conventional catheter needle 12 has a hollow tubular needle body 29 with a beveled front end 30 to facilitate hypodermic and intravenous insertion and has a tubular base portion 31 at the back end in communication with the interior bore of the needle portion 29. The front portion 32 of the needle base 31 is smaller in diameter than the remainder of the base and may be tapered to frictionally engage interior of the bore 23 of the catheter base 22. In some designs, the catheter base and the front portion of the needle base may be provided with conventional Leur lock threads to make a threaded connection rather than using frictional engagement. The exterior of the needle base portion 31 may be provided with a circumferential raised bead 33 or otherwise configured to receive a protective sheath (not shown). The rear portion of the needle base 31 has an interior bore 34.

The plug 13 has a reduced diameter forward portion 35 which may be tapered to frictionally engage the bore 34 at the rear end of the needle base 31 and an enlarged diameter rear portion 36 which has flat surfaces 37 on its exterior to facilitate griping with the fingertips to remove the plug from the needle. The 13 plug is also usually provided with a small interior bore 38.

Figure 5:
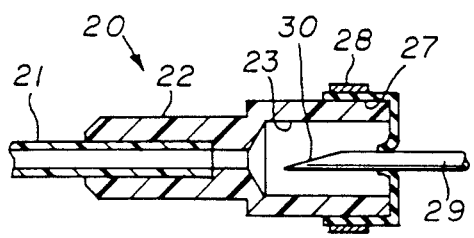
FIG. 5 is a partial longitudinal cross section of the present intravenous catheter fitting showing the end of a needle passing through the protective membrane seal.
Figure 6:
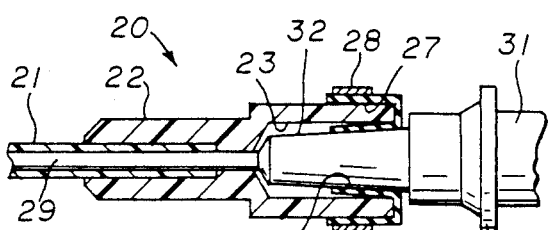
FIG. 6 is a partial longitudinal cross section of the present intravenous catheter fitting showing the base portion of a needle received in the connection end of the catheter base.

As shown in FIGS. 5 and 6, to assemble the needle 12 into the present catheter 20, the beveled front end 30 is pushed through the membrane seal 26 and due to the elasticity of the membrane material, the beveled needle portion will puncture the seal 26 as it passes through and will not tear the membrane, but will stretch as the forward motion of the needle continues and conform to the profile of the tapered front portion 32 of the needle base 31 and allow it to engage the interior of the catheter bore 23. Thus, the needle 12 may be inserted into the catheter 20 in the usual manner. The membrane seal 26 will facilitate the frictional engagement. Once in place, the needle and catheter may be used just as any standard catheter-needle assembly. It should be understood, that other intravenous tubular members other than needles may also be installed in the end of the catheter with the seal in place. If a threaded connection is used, the elastic characteristics of the membrane material will also conform to the threads allowing a threaded connection to be made without damage to the membrane.

When the needle 12 is withdrawn from the catheter 20, the membrane seal 26 resumes its original position (FIG. 4), except that it has a very tiny hole where the needle penetrated. The resilient material of the membrane seal will usually close the hole to a diameter so small that under normal use conditions, no leakage occurs. For example, the pressure of blood in a vein is usually 30-40 mm. of mercury, and the hole is so tiny that the pressure will not force the blood through the hole in the membrane seal.

OPERATION

In the assembled and packaged condition, the needle 12 is installed in the catheter 20 with the needle portion 29 and 30 penetrating the membrane seal 26 and the forward portion 32 of the needle base 31 engaged in the interior bore 23 of the catheter base 22 (FIG. 6) and the plug 13 frictionally engage in the bore 34 at the rear end of the needle base 31. The conventional protective sheath (not shown) is received over the catheter and engaged on the flange or raised bead 33 of the needle base. The interior diameter of the catheter flexible tubular front portion 21 closely surrounds the forward portion 29 of the needle but allows axial sliding movement of needle therethrough. The length of the catheter flexible tubular portion 21 is slightly shorter than the needle portion 29 s that the beveled, pointed end 30 of the needle 12 is exposed to facilitate intravenous insertion of both the needle and flexible tubular portion 21 of the catheter (FIG. 1).

In using the present catheter 20, the catheter assembly is removed from its package and the protective sheath is removed. In the assembled condition, the beveled end 30 of the needle 12 having the tubular portion 21 of the catheter surrounding its length is inserted into the vein. Since the membrane seal 26 fits around the needle exterior, when the vein is penetrated, blood will flow into the needle and will be visible in the base portion 31 of the needle and will also be drawn into the small bore 38 of the plug 13 due to capillary action in the normal manner. This visible detection of the fluid will signal that a suitable penetration has been made.

While the catheter 20 is held stationary, the plug 13 is removed from the needle 12 or the needle is withdrawn from the catheter 20. When the needle 12 is withdrawn from the catheter 20, the membrane seal 26 resumes its original position (FIG. 4), except that it has a very tiny hole where the needle penetrated. The resilient material of the membrane seal will usually close the hole to a diameter so small that under normal use conditions, no leakage occurs. For example, the pressure of blood in a vein is usually 30-40 mm. of mercury, and the hole is so tiny that the pressure will not force the blood through the hole in the membrane seal.

The person installing the catheter 20 can then take as much time as necessary to connect another tubular fitting to the open rear end of the catheter to complete the fluid injection or withdrawal procedure without the danger of the body fluids leaking through the catheter. If necessary, the person installing or removing the catheter can even use both hands to effect the connection.

Thus, there is no danger from exposure to free flowing body fluids during the interval between the time the needle is withdrawn from the catheter and the open end is connected. Since, there is no leakage under normal conditions, the person installing the catheter has plenty of time, and both hands available, to properly replace the protective sheath over the used needle and to properly dispose of the needle without the risk of losing the needle.

The present catheter having the membrane seal will automatically seal at the open end to prevent fluid leakage when a needle or fitting is removed and would still allow connection of the catheter to other devices with the seal in place. If a threaded connection is used, the elasticity characteristics of the membrane material will also conform to the threads allowing a threaded connection to be made without damage to the membrane.

While this invention has been described fully and completely with special emphasis upon a preferred embodiment, it should be understood that within the scope of the appended claims the invention may be practiced otherwise than as specifically described herein.

I claim:

1. An intravenous catheter assembly for fluid injection or withdrawal comprising
   a tubular fluid handling fitting having a fluid passageway therethrough with a tubular front extension sized for insertion into a vein and an opening at the rear end for connection to fluid injection or withdrawal means, and
   a resilient flexible membrane seal on said fitting effectively covering said rear end opening,
   said seal being sufficiently elastic to allow penetration thereof by a needle when inserted into said opening, and resuming its initial position after withdrawal of the needle to substantially close the penetration hole to prevent appreciable leakage of fluid from said rear end opening, and further including
   a connector connected to fluid injection or withdrawal means and fitted into said rear end opening and through said membrane opening, said membrane opening being stretched to surround said connector and contractible to seal against blood leakage when said connected is removed.

2. An intravenous catheter assembly according to claim 1 including
   a hypodermic needle inserted through said flexible membrane seal and through said tubular front extension with the end of the needle exposed to permit insertion of the needle and tubular extension together into a vein,
   said membrane seal having the opening made by said needle stretched to surround the rear portion of said needle, whereby
   after insertion into a vein, said needle may be disconnected and withdrawn from said catheter fitting to leave only said catheter tubular front end portion hypodermically and intravenously installed and allowing said resilient flexible membrane seal to contract to its original position with said membrane opening substantially closed to prevent leakage of blood therethrough.

3. An intravenous catheter assembly according to claim 1 in which
   said flexible membrane seal is heat sealed to the rear end surface of said fitting surrounding said rear opening therein.

4. An intravenous catheter assembly according to claim 1 in which
   said flexible membrane seal is adhesively sealed to the rear end surface of said fitting surrounding said rear opening therein.

5. An intravenous catheter assembly according to claim 1 in which
   said flexible membrane seal is stretched over the rear end surface of said fitting surrounding said rear opening therein and secured to a side wall of said fitting.

6. An intravenous catheter assembly according to claim 1 in which
   said flexible membrane seal is stretched over the rear end surface of said fitting surrounding said rear opening therein and secured by a clamping ring to a side wall of said fitting.

7. An intravenous catheter assembly according to claim 1 in which
   said fitting has a flat rear end surface and a peripheral flange surrounding said rear opening, and
   said flexible membrane seal is adhesively sealed to said flat rear end surface.

8. An intravenous catheter assembly according to claim 1 in which
   said fitting has a flat rear end surface and a peripheral flange surrounding said rear opening, and
   said flexible membrane seal is stretched over said peripheral flange surrounding said rear opening therein and secured to a side wall of said fitting.

9. An intravenous catheter assembly for fluid injection or withdrawal comprising
   a tubular fluid handling fitting having a fluid passageway therethrough with a tubular front extension sized for insertion into a vein and an opening at the rear end for connection to fluid injection or withdrawal means, and
   a resilient flexible membrane seal on said fitting effectively covering said rear end opening,
   said seal being sufficiently elastic to allow penetration thereof by a needle when inserted into said opening, and resuming its initial position after withdrawal of the needle to substantially close the penetration hole to prevent appreciable leakage of fluid from said rear end opening.
   a hypodermic needle inserted through said flexible membrane seal and through said tubular front extension with the end of the needle exposed to permit insertion of the needle and tubular extension together into a vein,
   said hypodermic needle having a connector for connection to a fluid injection or withdrawal means supporting the needle for insertion and withdrawal into and out of said tubular extension,
   said fitting having said rear opening sized to receive said connector,
   said membrane seal having the opening made by said needle stretched to surround the rear portion of said needle and said connector, whereby
   after insertion into a vein, said needle and connector may be disconnected and withdrawn from said catheter fitting to leave only said catheter tubular front end portion hypodermically and intravenously installed and allowing said resilient flexible membrane seal to contract to its original position with said membrane opening substantially closed to prevent leakage of blood therethrough.

10. An intravenous catheter assembly for fluid injection or withdrawal comprising a tubular fluid handling fitting a fluid passageway therethrough with a tubular front extension sized for insertion into a vein and an opening at the rear end for connection to fluid injection or withdrawal means, and a resilient flexible membrane seal on said fitting effectively covering said rear end opening, said seal being sufficiently elastic to allow penetration thereof by a needle when inserted into said opening, and resuming its initial position after withdrawal of the needle to substantially close the penetration hole to prevent appreciable leakage of fluid from said rear end opening, a hypodermic needle inserted through said flexible membrane seal and through said tubular front extension with the end of the needle exposed to permit insertion of the needle and tubular extension together into a vein, said hypodermic needle having a connector for connection to a fluid injection or withdrawal means supporting the needle for insertion and withdrawal into and out of said tubular extension, said fitting having said rear opening sized to receive said connector, said membrane seal having the opening made by said needle stretched to surround the rear portion of said needle and said connector, whereby after insertion a vein, said needle and connector may be disconnected and withdrawn from said catheter fitting to leave only said catheter tubular front end portion hypodermically and intravenously installed and allowing said resilient flexible membrane seal to contract to its original position with said membrane opening substantially closed to prevent leakage of blood therethrough, and further including a second connector and tubing associated therewith for transferring fluid to or from said fitting, said second connector being fitted into said rear opening after removal of said needle connector with said membrane opening stretched to surround said second connector to permit transfer of fluid to or from said fitting.

* * * * *